(12) United States Patent
Murakami et al.

(10) Patent No.: US 7,869,644 B2
(45) Date of Patent: Jan. 11, 2011

(54) METHODS OF AND APPARATUS FOR INSPECTING SUBSTRATE

(75) Inventors: Kiyoshi Murakami, Kyoto (JP); Masato Ishiba, Kyoto (JP); Jun Kuriyama, Fukuchiyama (JP); Teruhisa Yotsuya, Kyoto (JP)

(73) Assignee: OMRON Corporation, Kyoto (JP)

( * ) Notice: Subject to any disclaimer, the term of this patent is extended or adjusted under 35 U.S.C. 154(b) by 977 days.

(21) Appl. No.: 11/186,151

(22) Filed: Jul. 20, 2005

(65) Prior Publication Data

US 2006/0018531 A1    Jan. 26, 2006

(30) Foreign Application Priority Data

Jul. 21, 2004    (JP)    ............................. 2004-213512
Jul. 13, 2005    (JP)    ............................. 2005-203886

(51) Int. Cl.
  *G06K 9/00*    (2006.01)
  *G06K 9/48*    (2006.01)
  *G06K 9/36*    (2006.01)
  *H04N 7/18*    (2006.01)
  *B23P 19/00*   (2006.01)

(52) U.S. Cl. ....................... 382/147; 382/199; 382/286; 348/87; 29/739

(58) Field of Classification Search ................. 382/145, 382/147, 199, 286; 29/739; 348/87
See application file for complete search history.

(56) References Cited

U.S. PATENT DOCUMENTS 4,953,100 A  *  8/1990  Yotsuya ....................... 382/147
5,272,761 A  * 12/1993  Kanai et al. .................. 382/147
6,542,630 B1 *  4/2003  Sherwood .................... 382/147
6,633,663 B1 * 10/2003  Slesinger ..................... 382/147
2004/0049758 A1*  3/2004  Ueda et al. .................... 716/15
2006/0041535 A1*  2/2006  Qamhiyah et al. ............. 707/3

FOREIGN PATENT DOCUMENTS

| EP | 0263473 | 4/1988 |
| EP | 1388738 | 2/2004 |
| JP | 05035849 | 2/1993 |
| JP | 09-145334 | 6/1997 |
| JP | 11-344448 | 12/1999 |
| JP | 2002261500 | 9/2002 |
| JP | 2002271099 | 9/2002 |
| JP | 2003-008295 | 1/2003 |
| JP | 2004-053369 | 2/2004 |

OTHER PUBLICATIONS

European patent application No. 05015551.4-2204, European Search Report dated Nov. 22, 2005.
JP patent application No. 2005-203886, Examination Report mailed May 13, 2008.

* cited by examiner

*Primary Examiner*—Kathleen S Yuan
(74) *Attorney, Agent, or Firm*—Weaver Austin Villeneuve & Sampson LLP

(57) ABSTRACT

Inspection apparatus are used to inspect a substrate as solder is printed, components are mounted and the substrate is heated for a soldering process. Images of the substrate are taken both before and after a production process such as the component mounting process and the soldering process and their differences are extracted. Each component on the substrate may be identified by differentiation and binarization processes and setting conditions for windows are determined corresponding to identified components. Windows are set according to determined setting conditions for inspecting the conditions of the substrate by using image data in the set windows and standard inspection data corresponding to component identification data.

5 Claims, 12 Drawing Sheets

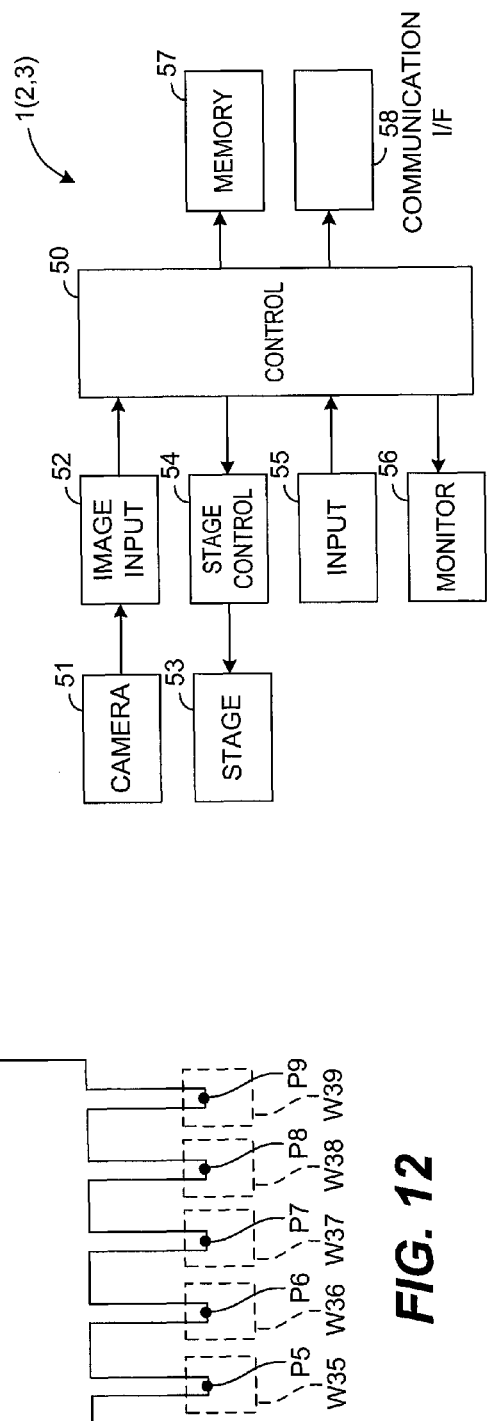
FIG. 14
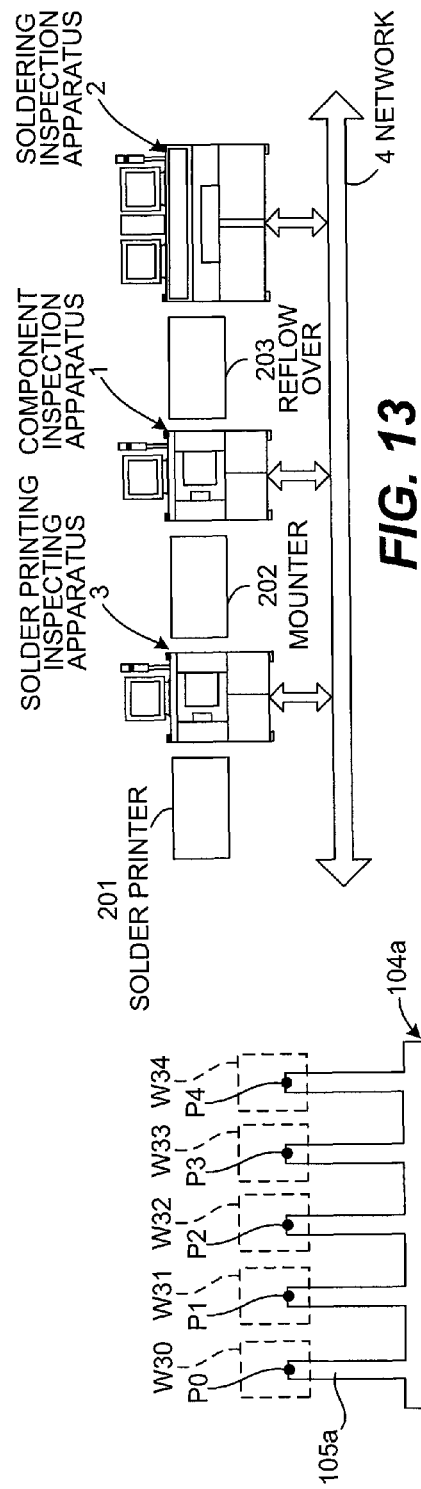
FIG. 13
FIG. 12

METHODS OF AND APPARATUS FOR INSPECTING SUBSTRATE

Priority is claimed on Japanese Patent Applications 2004-213512 filed Jul. 21, 2004 and 2005-203886 filed Jul. 13, 2005.

BACKGROUND OF THE INVENTION

This invention relates broadly to the inspection of a printed circuit board (hereinafter referred to simply as a substrate), or methods of and apparatus for inspecting a substrate whether during its production process or after it has been produced, inclusive of methods of determining conditions for setting an inspection window and creating inspection data for the purpose of inspecting the conditions of various mounted components and soldering.

Substrates with components mounted thereto are usually produced by sequentially carrying out the process of printing cream solder on a printed circuit board (or the solder printing process), the process of mounting components at positions coated with the cream solder (or the component mounting process) and the process of heating the circuit board thereafter to solder the components thereonto (or the soldering process). It is also a common practice to carry our an inspection after each of these production processes is performed in order to check whether or not any defective products have been produced.

Representative examples of apparatus for carrying out such inspections include those making use of the image processing technology whereby conditions for setting a window for inspecting target components (inclusive of their positions and sizes), binarization threshold values for extracting targets of inspection and judgment standards for determining appropriateness of extracted inspection targets are registered. In what follows, such registered data are summarily referred to as inspection data.

The conditions for setting an inspection window change, depending upon factors such as the purpose of the inspection and the target of inspection. In the case of an inspection after the component mounting process, for example, the purpose of the inspection is to discover the absence of a component or the presence of a wrong component and hence an inspection window approximately of the same size as the intended component is set at the intended position of the component. In the case of an inspection after the soldering process, inspection windows are set individually for the lands in order to inspect the shapes of the solder fillets formed thereon.

Examples of prior art method for determining the conditions for setting an inspection window include that of displaying an image of a model substrate, receiving a specification (say, by the operation of a mouse) on the displayed image and using the position and the size of the specified region as set conditions, as well as a method of using CAD data of the substrate. For determining the setting conditions of a window for inspecting a component, for example, an inspection window may be automatically pasted on the CAD data by using frame data of the component registered in the CAD data (representing an outline of the component) such that the position and the size of this window may be treated as setting conditions. Japanese Patent Publication Koho 2,570,239 discloses a combination of a component library registering standard inspection data for each component and design data on substrates such as CAD data for automatically generating data inclusive of inspection data other than the setting conditions for inspection windows.

Methods of setting conditions for an inspection window according to a user's operation for specification are troublesome because of a large amount of work that comes to be involved. Methods of using CAD data to determine setting conditions for an inspection window are also disadvantageous because the frame data on components found in the CAD data may not necessarily be representing the true size of the component and a manual correction may become necessary on a pasted window.

The method of aforementioned Japanese Patent Publication Koho 2,570,239 is to correlate mounted position of each component of the substrate in CAD data with the standard inspection data in a component library but the keys for the correlation may not match between the two. While the CAD data are created as individual data for each component number and are capable of identifying the mounted components, the component library classifies components with similar shapes and functions into a group called "variation" and data are registered in units of variations. Thus, a table becomes necessary for correlating these two sets of data in order to identify a variation corresponding to a given CAD data item and hence the process becomes complicated and cumbersome, and inspection data cannot be created efficiently.

SUMMARY OF THE INVENTION

It is therefore an object of this invention in view of the above to easily determine conditions for setting an inspection window by using an image taken of an actual substrate.

It is another object of this invention to provide a simpler method than prior art methods for combining CAD data and a component library for obtaining inspection data for the inspection of components.

The invention firstly relates to a method of determining setting conditions for a window for the inspection of a substrate which may be in the process of production or a finished product, and the method may be characterized as carrying out the following three steps which are hereinafter conveniently referred to as a first step, a second step and a third step. The first step is carried out on a substrate after it has undergone a specified one of a plurality of sequentially performed production processes for producing a mounted substrate and includes the step of taking and thereby obtaining a first image of this substrate. The second step is for taking and thereby obtaining a second image of the same substrate after a next one of these production processes has been performed thereon. In the third step, differences between these two images are extracted and setting conditions for a window for inspecting a specified target area on this substrate are determined by using these extracted differences.

In the above, the setting conditions of a window may be generally interpreted as being data that represent the position and the size of the window. Examples of the plurality of sequentially performed production processes for producing a mounted substrate may include a solder printing process, a component mounting process and a soldering process. In such a case, the first step may be carried out after the solder printing process and the second step may be carried out after the component mounting process. Alternatively, they may be carried out respectively after the component mounting process and the soldering process.

The third step may comprise the steps of creating a differential image by obtaining differences in grading between mutually corresponding pixels on the two images and carrying out a process such as binarization and edge extraction on this differential image. The differences herein extracted may be considered to correspond to the changes made on the substrate during the production process that was carried out between the two steps.

The method as generally described above may be explained further in detail next by way of the following three embodiments.

According to a first embodiment, the first step takes place after the solder printing process and the second step takes place after the component mounting process. In this case, the differences extracted in the third step may be considered to correspond to the structures added to the substrate in the component mounting process, or a component or components. Thus, setting conditions for a window, or windows, for the component inspection are determined based on the positions and sizes of the areas where the differences have been extracted.

By this embodiment, the second image may be taken after an image is obtained from a substrate in a good solder printing condition and it is ascertained that components have been properly mounted, and the two images may be used to determine setting conditions for windows for inspecting components. If the setting conditions thus obtained are registered in a memory, they may later be used conveniently whenever substrates of the same kind are to be inspected.

In summary, since setting conditions for windows for the inspection of components can be automatically extracted according to this invention, it becomes unnecessary to carry out operations for specifying an inspection area or to use CAD data and the burden on the user becomes significantly reduced.

It is desirable for a window for the inspection of a component to be of a size suitable for the inspection, including an area where the differences are extracted such as a rectangle that circumscribes it externally. It is also desirable not to set any window if the area where the differences are extracted is smaller than the size of the smallest component.

If a component used in the second step is mounted under a displaced condition, the window for the inspection also becomes displaced and it becomes impossible to accurately determine its setting conditions. In such a case, it is preferable to carry out the steps of extracting an area printed with cream solder from the image of the substrate after the solder printing process and correcting the position of the window for the component inspection based on its positional relationship with respect to the area printed with cream solder. If these steps are carried out in the third step, the setting position of the window can be properly corrected to where this component should properly be mounted.

According to a second embodiment, the first step takes place after the component mounting process and the second step takes place after the soldering process. In this case, the differences extracted in the third step may be considered to correspond to the changes brought about by the melting of the cream solder on the lands. Thus, setting conditions for a window, or windows, for the inspection of soldering condition are determined based on the positions and sizes of the areas where the differences have been extracted. In this case, it is desirable to make the window to be rectangular, externally circumscribing the extracted area or to be somewhat larger.

By this embodiment of the invention, too, setting conditions of windows can be automatically extracted by taking images of a substrate and by using the two obtained images. Since windows for the inspection of soldering must be set individually for separate lands, they are expected to be smaller and more numerous that windows for the inspection of components. Thus, automatic extraction of these windows can even more significantly reduce the burden on the user.

Although printed solder may be displaced from or spill over out of a land, the surface tension may serve to pull back the solder back into the area of the land. In such a case, the area in which the differences are extracted may become expanded beyond the area of the land and the extracted area may become displaced from or larger than the land. In view of this, it is desirable to carry out the steps of extracting from the image of the substrate after the soldering process an area where the basic color of the substrate appears and correcting the window for the inspection of soldering based on the extracted area with the basic color of the substrate.

In the above, the area where the basic color of the substrate appears may be considered to correspond to the surface of the main body of the substrate where there is no component or land. Such an area can be extracted by a process such as binarization with the use of a preliminarily specified threshold value on the image of the substrate after the soldering process. By this correction process on the window, portions of the window overlapping with the area with the basic color of the substrate may be deleted and the width of the window may be enlarged such that the boundary of the window will approach the boundary with the area with the basic color of the substrate. By such a correction process, setting conditions of an inspection window can be determined accurately even if there is an error in the printed area of the solder.

According to the third embodiment, like the first embodiment, the first step takes place after the solder printing process and the second step takes place after the component mounting process. In the third step, however, setting conditions of a window for the inspection of soldering are determined by using as a standard a specified characteristic point contained in the difference extracted between the two images.

When the soldering condition is inspected on an IC having a plurality of electrode parts (leads), for example, it is necessary to set a window in an area containing the land corresponding to each of the leads. In such a case, too, if an image of the substrate after the solder printing process and another taken after the component mounting process are used, it is possible to set an inspection window for each land by extracting the image of the component as a whole and thereafter extracting a characteristic point for each lead such as its tip.

According to the method described above, images are taken of a specified substrate twice, that is, after a specified production process has been carried out and after the next production process has been carried out, and setting conditions of a window used for inspection can be automatically determined from these images. Thus, the burden on the user can be significantly reduced. Since inspection windows can be set based on a structure actually added to the substrate or a portion that has been changed, the setting conditions can be determined with a high level of accuracy.

After setting conditions are determined by using a single substrate, this result may be registered and used again when another substrate of the same kind is to be inspected. Setting conditions may also be determined for individual substrates, for example, when fluctuations in positions and sizes of components and lands are considered to be relatively large. When this inspection method is applied for the inspection of components, however, if there is a component that is absent, it becomes impossible to set a window. It is desirable therefore to separately carry out a process such as a matching process with component position data in CAD data regarding the number of windows to be set or their positions.

The invention also relates to another method for determining setting condition for an inspection window, characterized as comprising a first step of registering standard inspection data including size data on various component types, a second step of taking and thereby obtaining a first image of the substrate before the component is mounted thereto, a third step of taking and thereby obtaining a second image of the substrate after the component is mounted thereto, a fourth step of extracting differences between the first and second images, comparing size of each of areas in which these differences are extracted with the size data in the standard inspection data and thereby identifying a corresponding component, and a fifth step of determining setting conditions for the window based on position and size of area where the corresponding component was identified in the fourth step.

The standard inspection data on various component types in the above may be considered as corresponding to the aforementioned component library. By this method, after differences are extracted between the images taken before and after the components are mounted, the size of each area where the differences are extracted is compared with the size data in the standard inspection data such that a component for which the size difference is less than a certain threshold value can be identified as the component corresponding to the area and a window for inspecting the component can be set for this area.

By this method, an area corresponding to a component can be identified accurately by matching the magnitude of difference extracted between the two images with the sizes of various components such that setting conditions of a window for inspecting a component can be more accurately determined. When such setting conditions are registered for the purpose of inspection, it is preferable to do so in correlation with the data in the fourth step for showing the result of component identification (such as data for indicating component types). In this way, an inspection may be carried out for each window by using the standard inspection data of the corresponding component after the inspection window is set based on the setting conditions registered in the image of the substrate after components have been mounted.

The invention further relates to methods of inspecting soldered conditions of a substrate. One example of these methods may be characterized as comprising a first step of taking and thereby obtaining a first image of the substrate after a soldering process is carried out thereon, a second step of taking and thereby obtaining a second image of the substrate prior to the soldering process, a third step of extracting differences between the first and second images and determining setting conditions of a window for inspection of the soldering condition based on position and size of area where these differences are extracted and a fourth step of setting the window on the first image based on the setting conditions determined in the third step and carrying out an inspection of the soldering condition by using image data inside this window.

In the above, the image of the substrate before the soldering process may be the same image referred to earlier above as the image after the component mounting process. Thus, the image used for the inspection of the mounted condition may be saved and used again for the purpose of this method. This, however, is not intended to limit the scope of the invention and an image may be taken immediately before the soldering process is carried out and saved until the time of the inspection. By this method, since an inspection window is set for each target substrate to be inspected, the accuracy of inspection can be kept high even if there are fluctuations in the positions and sizes of lands among different substrates.

Another example of these methods may be characterized as comprising a first step of registering mounted component data showing positions and types of components on the substrate and standard inspection data related to inspection of soldering conditions for various component types, a second step of taking and thereby obtaining a first image of the substrate after a soldering process is carried out thereon, a third step of taking and thereby obtaining a second image of the substrate prior to the soldering process, a fourth step of extracting differences between the first and second images, a fifth step of identifying areas corresponding to each of the components on the substrate by comparing position data of each of the components having the mounted component data registered with the position of the area in which the differences are extracted in the fourth step, a sixth step of determining setting conditions of a window for inspection of the soldering condition based on position and size of the area identified in the fifth step, and a seventh step of setting the window on the first image based on the setting conditions determined in the sixth step and carrying out an inspection of the soldering condition by using image data inside the window and the standard inspection data of component corresponding to the window.

In the above, the standard inspection data may be a component library. The mounted component data may be created from substrate design data such as CAD data but may be obtained also from an inspection apparatus for the mounted condition of components. Data indicative of the setting position of the window for the inspection of components and the component corresponding to the window may be obtained as mounted component data. In such a case, the inspection may be started after mounted component data are received from the inspection apparatus for mounted conditions of components and registered.

In the fifth step described above, the area closest to the component among those where differences are extracted in the fourth step may be correlated to each of the mounted components on the substrate. In this case, as many areas as there are of soldered area may be correlated but since the standard inspection data include those indicative of the shape of each component type, number of lands for each component and relative positional relationships, they may be referenced for recognizing an area to be correlated to each of the components.

In the sixth step described above, windows for inspecting soldered conditions are set based on positions and sizes of correlated areas such that the inspection windows can be variably set according to the actual soldered areas while the standard inspection data can be used for the others. Thus, inspections can be carried out efficiently and accurately according to the fluctuations in the positions and sizes of the lands.

When these methods are used, it is desirable to extract from the image of the substrate after the soldering process areas showing the basic color of the substrate and to correct the setting conditions of the windows for the inspection of soldering conditions based on the results of extraction of such areas.

The invention further relates to a method of creating inspection data for the inspection of a substrate, characterized as comprising a first step of registering standard inspection data including size data of components of various types, a second step of taking and thereby obtaining a first image of the substrate before components are mounted thereto, a third step of taking and thereby obtaining a second image of the substrate after components are mounted thereto, a fourth step of extracting differences between the first and second images, comparing size of each of areas in which the differences are extracted with the size data in the standard inspection data and thereby identifying a corresponding component, and a fifth step of determining setting conditions for a window based on position and size of area where the corresponding component was identified in the fourth step and creating inspection data by correlating the standard inspection data of the corresponding component with the window.

The invention further relates to apparatus for inspecting mounting conditions and soldered conditions of a substrate. The former may be characterized as comprising a first image input means for inputting a post-mounting image of the substrate after components are mounted thereto, a second image input means for inputting a pre-mounting image of the substrate before these components are mounted thereto, a differentiating means for extracting differences between the post-mounting image inputted by the first image input means and the pre-mounting image inputted by the second image input means, a condition determining means for determining setting conditions of a window based on positions and sizes of areas where the differences are extracted by the differentiating means, a memory for storing the setting conditions determined by the condition determining means, a window setting means for setting the window on the post-mounting image based on the setting conditions stored in the memory when the post-mounting image is inputted by the first image input means, and an inspecting means for inspecting the components by using image data in the window set by the window setting means. The latter may be characterized as comprising a first image input means for inputting a post-reflow image of the substrate after a soldering process is done on the substrate, a second image input means for inputting a pre-reflow image of the substrate taken and thereby obtained before the soldering process is done on the substrate, a differentiating means for extracting differences between the post-reflow image inputted by the first image input means and the pre-reflow image inputted by the second image input means, a window setting means for setting a window on the post-reflow image based on positions and sizes of areas where the differences are extracted by the differentiating means, and an inspecting means for inspecting soldering condition of the substrate by using image data in the window set by the window setting means.

In the above, the first and second image input means may each be formed as an image taking means for taking an image of the substrate, means including a camera interface and an A/D converter circuit for taking in images from the image taking means, an image reading means for reading out images stored in a memory device and an image data receiving means for receiving image data transmitted from another apparatus. According to a preferred embodiment of the invention, the first image input means is formed as means for accepting images from an image taking means and the second image input means is formed as means for receiving transmission of image data used by an apparatus on the upstream side.

The differentiating means, the window setting means, the inspection means and the condition determining means may each be formed as a computer having a corresponding program set therefor. Instead, a single computer may be used. Other means such as an application specific IC (ASIC) may be used for some of them.

BRIEF DESCRIPTION OF THE DRAWINGS

FIGS. 11 and 12 are drawings for explaining a method of creating setting data of land windows by using a component mounting apparatus.

FIG. 13 is a sketch of a production line for substrates.

FIG. 14 is a block diagram of any of the inspection apparatus shown in FIG. 13.

DETAILED DESCRIPTION OF THE INVENTION

Figure 1:
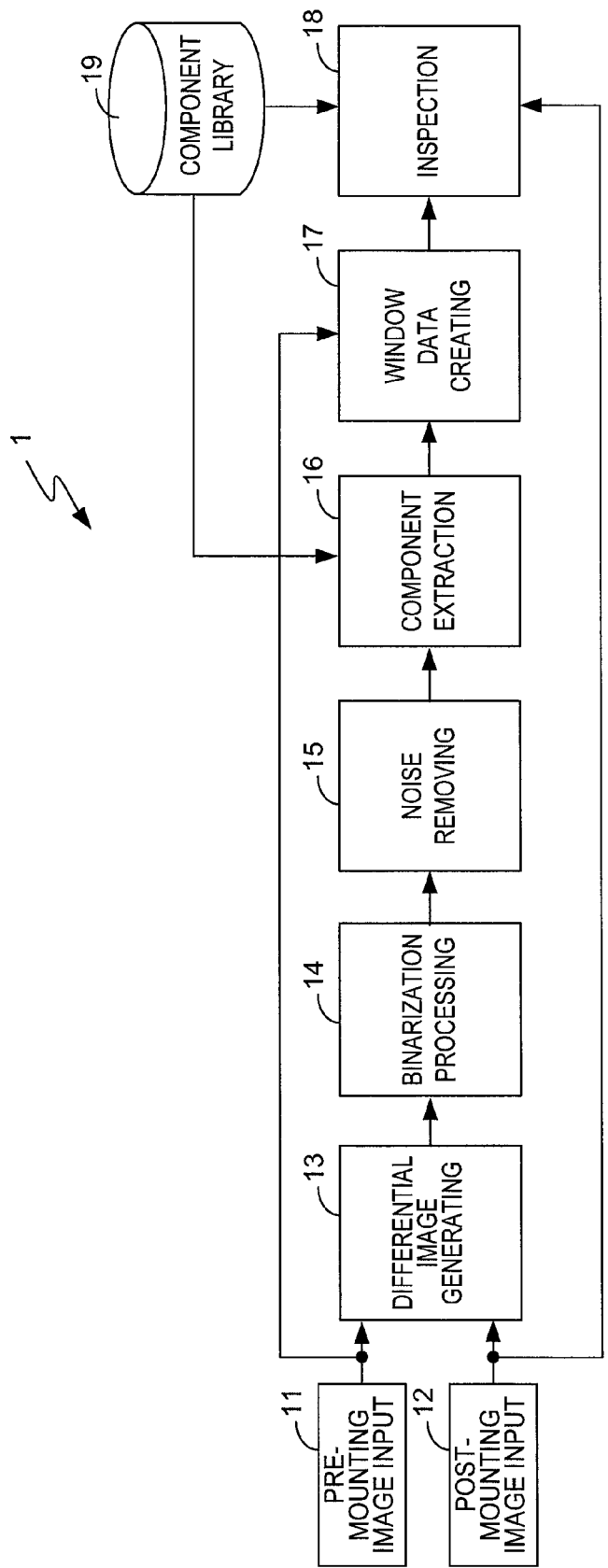
FIG. 1 is a functional block diagram of an apparatus for component inspection embodying this invention.

FIG. 1 shows the principal functions of a component inspection apparatus 1 according to an embodiment of this invention for inspecting a substrate after the component mounting process and before it is introduced into a reflow oven to check whether or not the mounting of the components has been carried out correctly such as regarding erroneous mounting, positional displacement and rotational displacement of components.

As shown, the component inspection apparatus 1 comprises an input part for substrate image before the mounting (pre-mounting image) 11, an input part for substrate image after the mounting (post-mounting image) 12, a differential image generating part 13, a binarization processing part 14, a noise removing part 15, a component extraction part 16, a window data creating part 17, an inspection part 18 and a component library 19 where standard inspection data on components of a plurality of different kinds are registered.

In the above, the post-mounting image is an image of the substrate after it has gone through the component mounting process, while the pre-mounting image is an image before the component mounting process has been carried out thereon, that is, the image taken thereof after the cream solder has been printed thereon. They are both a digital color image with color data r (red), g (green) and b (blue) combined together. It is to be assumed that the differences between these images regarding the position and the size of the substrate itself are already corrected.

The differential image generating part 13 is for calculating the differentials between the post-mounting image and the pre-mounting image and creating a differential image from the results of this calculation process. In this differentiation calculation process, differences are obtained for each of the color data r, g and b for each pair of corresponding pixels of the images and these differences are compared with a specified threshold value. If even one of the differences between the color data is greater than the threshold value for a pixel, data values reflecting the differential data of the colors are set for the pixel and the other pixel data values are set equal to zero to create the differential image such that portions having large color differences between the two images are reflected on the differential image. This differentiation calculation process may be carried out by obtaining differences in brightness, shade or color phase values, instead of color data, for each pixel.

The binarization processing part 14 is for using a suitable threshold value to binarize the differential image created by the differential image generating part 13, thereby creating a black-and-white image by blackening the portions with a large color difference and whitening the other portions. In the above, the choice between black and white may be reversed.

The noise removing part 15 is for removing noise by smoothing outlines and carrying out an expansion or contraction process on the binary image. The component extraction part 16 serves to carry out an outline-tracing process or a labeling process on the binary image after the noise removal to cut out and extract regions with black pixels.

Figure 2:
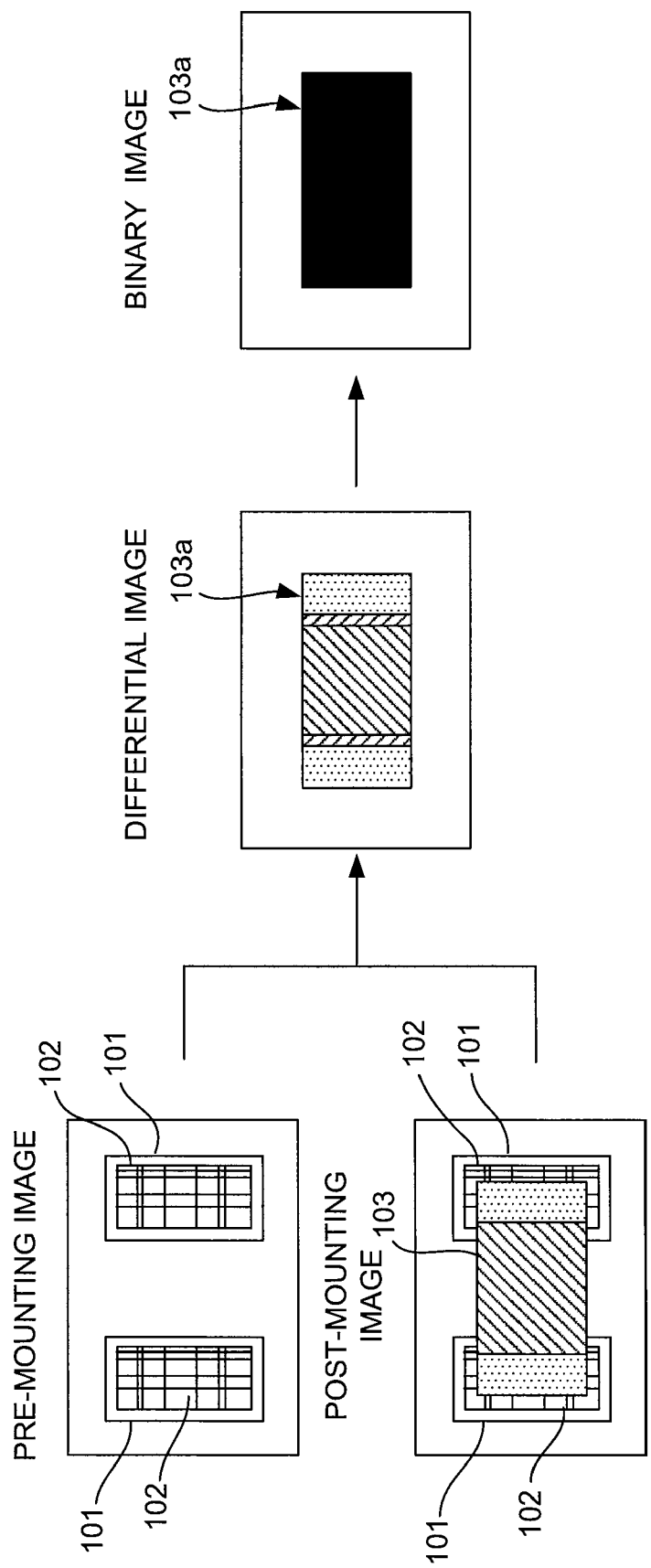
FIG. 2 shows an example of differential image and binary image obtained from a pre-mounting image and a post-mounting image of a specified component.

FIG. 2 shows an example of a pre-mounting image and a post-mounting image of a chip component as a representative example of mounted component, as well as a differential image and a binary image obtained therefrom. In FIG. 2 (and also thereafter), numerals 101 each indicate a land, numerals 102 each indicate an area coated with cream solder, and numeral 103 indicates a component. In the differential image, the changing colors are indicated by a difference in shading.

As explained above, the pre-mounting image is of a substrate printed with cream solder and the post-mounting image is of a substrate with a component or components mounted onto the cream solder. Thus, if a differentiation calculation is carried out between these two images, a specified color distribution can be extracted from an area (indicated by 103a) corresponding to the image 103 of a component (inclusive of the image of the electrode portions in addition to the image of the main body of the component) added in the component mounting process. Each pixel in this area 103a is converted uniformly into a black pixel by the binarization process, and the component extraction part 16 serves to extract this area 103a, or the image of the component.

The component library 19 has similar functions, components with only small differences in external appearances being collected in a group referred to as a variation and standard inspection data inclusive of size data on components and lands registered for each variation. Variations are each assigned a variation name as identification data.

The component extraction part 16 serves to sequentially compare the size of each black pixel area appearing on the binary image after the removal of the noise with the component size data of the variations in the component library 19 and to thereby determine the component variations corresponding to the black pixel areas. This process for determining a variation corresponding to a component is hereinafter referred to as the component identification process.

The window data creating part 17 serves to create data (hereinafter referred to as setting data) for showing setting conditions of inspection windows (hereinafter referred to as the component window) for each of the components specified by the component extraction part 16. According to the example herein illustrated, a rectangle (externally) circumscribing the black pixel area 103a corresponding to the component is set and the data for representing the position and the size of this rectangle (such as the coordinates of its left-hand top corner and right-hand bottom corner) may be used as the setting data of the component window.

The window data creating part 17 further serves to correlate the data indicative of the result of component identification by the component extraction part (hereinafter referred to as the component identification data) with the aforementioned setting data of the component window.

According to the present example, pre-mounting and post-mounting images are generated and the series of processes described above is carried out prior to the inspection for each substrate with the cream solder in a good printed condition and components in good mounted condition such that a combination is obtained for each component between setting data of component window and component identification data. Such combinations of data thus obtained are made into a file (referred to as a window setting file) in units of substrates and registered in a memory (shown at 57 in FIG. 14 to be described below).

At the time of an inspection, an image to be inspected is supplied from the input part 12 for post-mounting image to the inspection part 18, and the inspection part 18 serves to set a component window on the supplied post-mounting image on the basis of the setting data stored in the aforementioned window setting file. The inspection part 18 further serves to read out of the component library 19 the standard data corresponding to the component identification data combined with the aforementioned setting data and to carry out image processing and inspection by using these standard inspection data.

Figure 3:
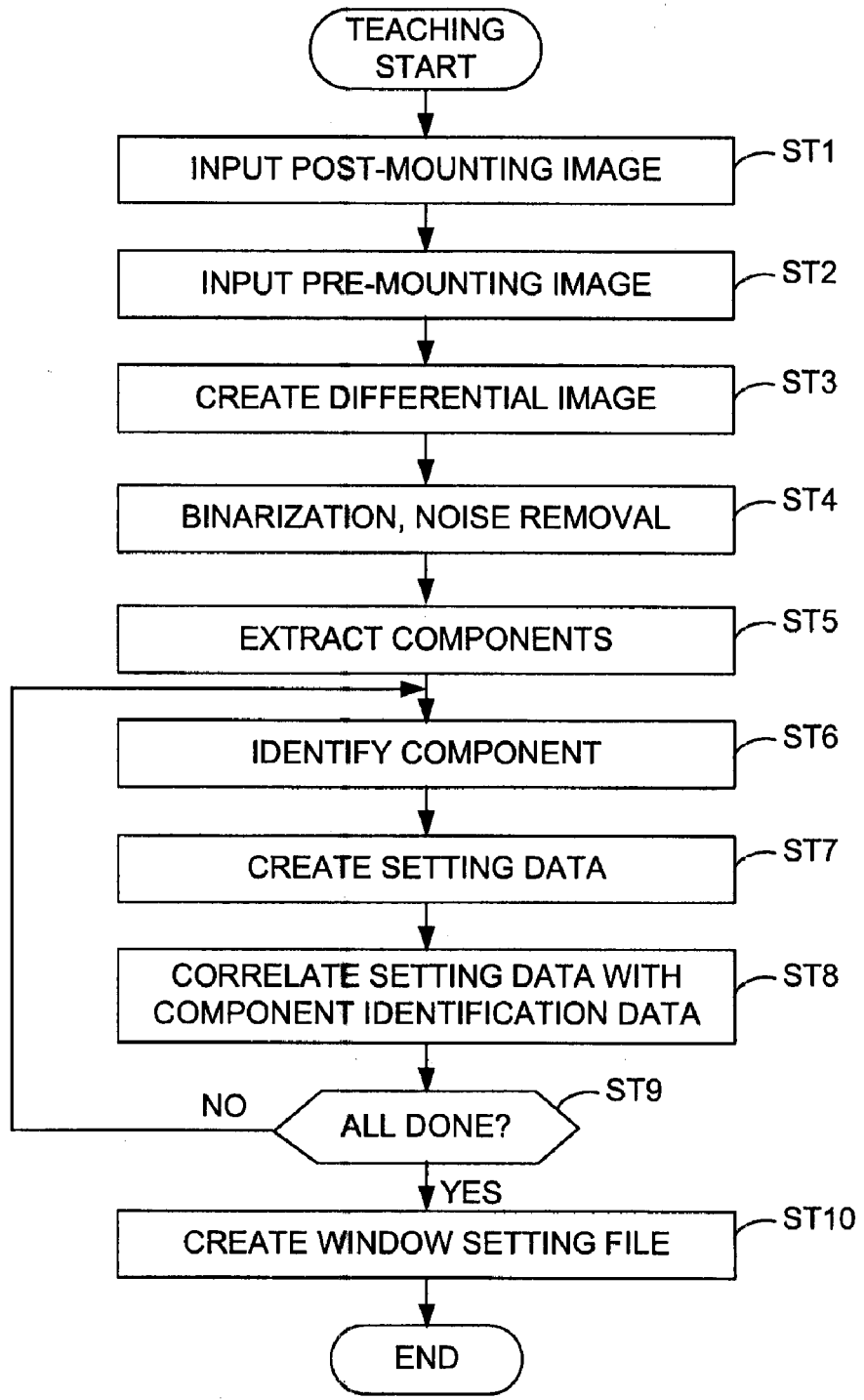
FIG. 3 is a flowchart of a routine of a teaching process for creating a window setting file.

FIG. 3 shows a teaching routine carried out by this component inspection apparatus 1. This teaching process is for the purpose of creating the aforementioned window setting file. Prior to the execution of this routine, an image of a specified substrate with cream solder in a good printed condition is taken to obtain a pre-mounting image and a component is thereafter mounted to this substrate. After it is ascertained that the mounting condition is correct, another image is taken thereof to obtain a post-mounting image.

The routine of FIG. 3 starts by inputting the aforementioned pre-mounting image (Step ST1) and then the post-mounting image (Step ST2). Next, a differential image is created by using these pre-mounting and post-mounting images (Step ST3) in a manner described above. This differential image is binarized and noise is removed (Step ST4). An outline-tracing process or a labeling process on the binary image with noise removed and a black pixel area corresponding to each component is extracted (Step ST5).

Steps ST6-ST8 are repeated for each of the extracted components. In Step ST6, the number of constituent pixels of the black pixel area is extracted as the size data for the component under consideration and is compared with the size data of the variations in the component library 19. If a variation is found with which the size difference is less than a specified error range, this variation is identified as corresponding to the component under consideration. The variation name of this identified variation is saved in a work memory (not shown).

After the component is identified, a rectangle that circumscribes this black pixel area is set and its position and size are extracted as the setting data of the component window (Step ST7) and the component identification data set in Step ST6 are correlated to the setting data (Step ST8).

After this series of Steps ST6-ST8 is completed for all of the components (YES in Step ST9), the combined data for the components are collected as the aforementioned window setting file and stored in a memory for registration (Step ST10).

In order to improve the accuracy of setting data for the component window in the process described above, it is desirable to initially obtain pre-mounting and post-mounting images of a plurality of substrates and to carry out aforementioned Steps ST3-ST9 for each substrate and to use the average of the setting data obtained for these substrates as the final setting data.

Although it was explained above, in order to simplify the description, that all components on the substrate are to be identified by using a binary image converted from a differential image, there are components that cannot be identified easily from the size data alone. Regarding such components, it is preferable to preliminarily teach their positions and to eliminate them from the processes of Steps ST6-ST9 or to cause the user to input a component type in Step ST6.

Next will be explained an inspection mode by the use of a window setting file registered by the teaching process as described above. At the time of this inspection, window setting files corresponding to the substrates to be inspected are read out and set in a work memory. The routine shown in FIG. 4 is carried out for each target substrate to be inspected to check the presence or absence of components as well as appropriateness of their mounting conditions.

Figure 4:
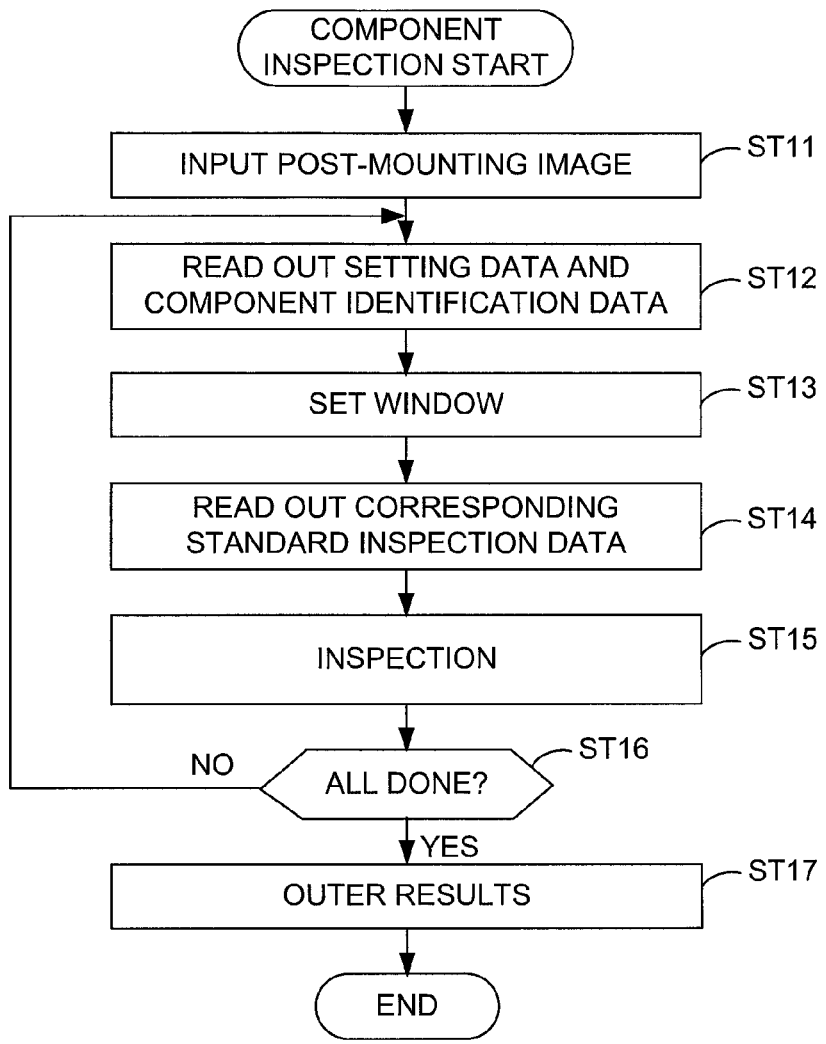
FIG. 4 is a flowchart of a routine for component inspection.

The routine of FIG. 4 starts by inputting the post-mounting image of the target substrate to be inspected (Step ST11) and then a first combination of setting data of component window and component identification data is read out (Step ST12). Next, a component window is set on the post-mounting image on the basis of the setting data read out in Step ST12 (Step ST13). Next, the standard inspection data corresponding to the component identification data are read out of the component library 19 (Step ST14), and the presence or absence of the component and the appropriateness of the mounting condition are inspected by processing the image in the component window set in Step ST12 by using the aforementioned standard inspection data (Step ST15). Examples of method for inspecting the presence or absence of a component include the method of determining the presence or absence of an area where the color of an electrode appears while the component window is scanned in the direction of the width of the component window. The appropriateness of the mounting condition may be judged by extracting the component by binarizing the image inside the component window and measuring its center of gravity or the angle of its principal axis.

The processes of Steps ST12-ST15 are carried out for each combination of all data set in the aforementioned window setting file. When the processing on the final combination of data is completed (YES in Step ST16), the result of the inspection is outputted (Step ST17) and this concludes the inspection for one of the mounted substrates.

By the teaching and inspection processes of FIGS. 3 and 4, the position and size of each component are extracted by using the pre-mounting and post-mounting images of a specified substrate such that the component on the substrate is identified and setting data of the component window are created corresponding to each component. By the inspection process of FIG. 4, furthermore, it is possible to set a component window on the basis of setting data and thereafter to carry out an inspection by reading out necessary standard inspection data from the component library 19 on the basis of the component identification data corresponding to the setting data. Thus, it becomes unnecessary to require the user to specify any area or to carry out a cumbersome process such as the correction on the window automatically extracted from CAD data. In other words, the present invention makes it possible to create setting data of a component window accurately and easily.

Although the example of FIG. 3 presumed the use of both pre-mounting and post-mounting images of good quality for creating the setting data of a component window, this is not intended to limit the scope of the invention. If at least the condition of solder printing on the substrate prior to the component mounting is good, the situation can be responded to even with some positional displacement of components on the substrate after the mounting.

Figure 5:
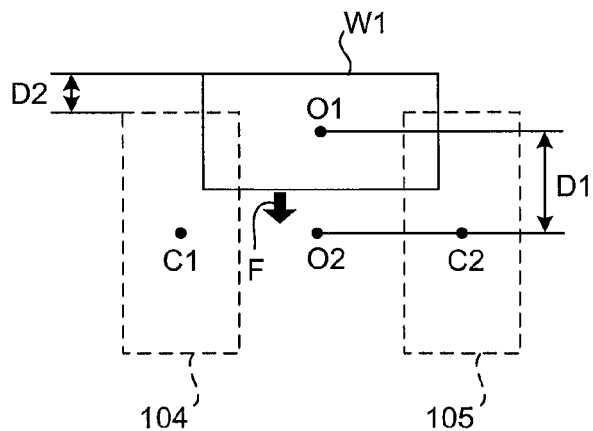
FIG. 5 is a drawing for explaining a method of correcting a component window.

FIG. 5 shows an example of response when a mounted component on the substrate is displaced. In this example, after a component window W1 is set by using the differential image of the pre-mounting and post-mounting images, the position of this component window W1 is corrected on the basis of the area printed with cream solder (hereinafter referred to as the soldering area).

In FIG. 5, W1 indicates a component window of a chip component and its center point is at $O_1$. Dotted rectangles 104 and 105 indicate soldering areas corresponding to lands on both sides, extracted by binarization of the aforementioned pre-mounting image by a color suitable to the cream solder.

In this example, after center points $c_1$ and $c_2$ are obtained for the soldering areas 104 and 105, the center point $O_2$ therebetween is obtained and the distance D1 between these two center points $O_1$ and $O_2$ is extracted. The distance D2 between the edge of the component window W1 and the corresponding edges of the soldering areas 104 and 105 is also extracted and these distances D1 and D2 are compared with a specified threshold value. If either of the distances D1 and D2 exceeds this threshold value, the position of the component window W1 is corrected such that this distance will become less than the threshold value. In the case of FIG. 5, it is desirable to move the component window W1 in the direction of arrow F such that the distance D1 will become less than the threshold value.

When a component is extracted from the image of an actual substrate and a component window W1 is set on the basis of the result of this extraction, as in the example described above, it becomes impossible to set the component window W1 at an appropriate position if the component undergoes a displacement. By the correction process shown in FIG. 5, however, the position of the component window W1 can be corrected appropriately because the position of the component window W1 can be corrected to another area where the component is appropriately mounted by using the soldering area as a standard.

Although FIG. 5 shows only the distance D2 as the distance between the component window W1 and the edges of the soldering areas 104 and 105, it is desirable to also measure the distance between the lower edges and to compare both distances with the threshold value. It is further desirable to correct the position of the component window W1 in the left-right direction similarly by using the soldering areas 104 and 105 as standards.

Figure 6:
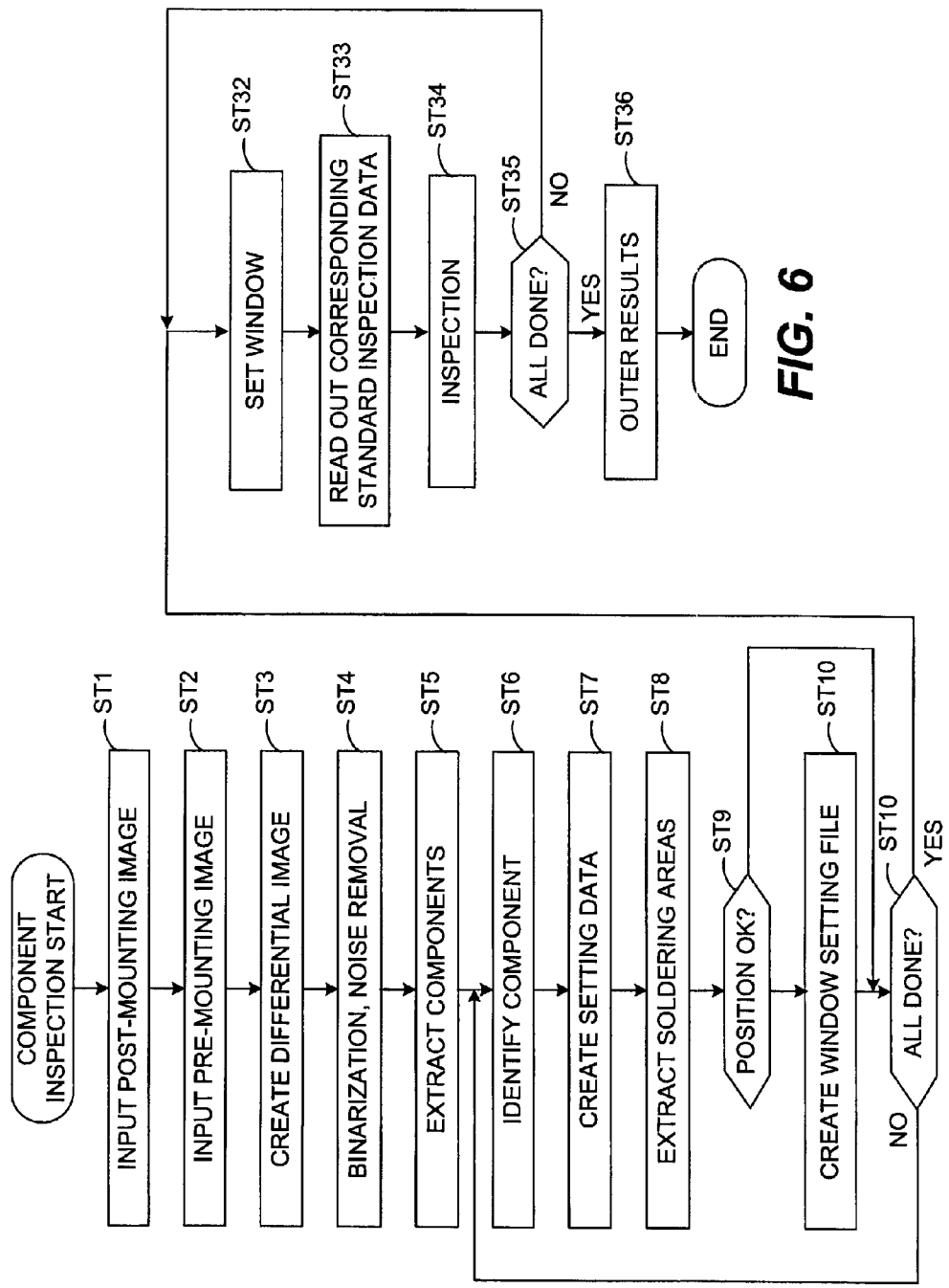
FIG. 6 is a flowchart of another routine for component inspection.

If the process according to FIG. 5 is introduced, when there is no need to consider the absence of a component or a large-scale displacement, component windows may be set for each substrate without registering the setting data of component windows and an inspection may be carried out at each component window by using the aforementioned standard inspection data. FIG. 6 shows a routine for processing in such a situation.

The routine of FIG. 6 starts by inputting a post-mounting image (Step ST21) and then a pre-mounting image (Step ST22). Step ST21 may be effected by inputting an image from a camera 51 to be described below and Step ST22 may be effected by inputting an image transmitted from another inspection apparatus although this does not limit the scope of the invention. Steps ST21 and ST22 may each be effected by inputting a preliminarily created and saved image.

Steps ST23-ST25 of FIG. 6 are similar to Steps ST3-ST5 explained above with reference to FIG. 3, and a black pixel area is extracted corresponding to each component.

Steps ST26-ST30 are repeated thereafter for each of the extracted components. In Step ST26, the component under consideration is identified by comparing the number of constituent pixels of the black pixel area corresponding thereto with the size data of components in the component library 19.

Next, setting data of the component window are created by the method of setting a rectangle circumscribing the black pixel area externally (Step ST27). As in the teaching process described above, the setting data are saved in the work memory in combination with data showing the result of component identification (component identification data) in Step ST26.

Next, an area of a specified size is set so as to include the black pixel area of the pre-mounting image and the soldering areas 104 and 105 shown in FIG. 5 are extracted by binalizing the image inside this area (Step ST28). Next, it is judged to determine whether the component window set in Step ST27 is at an appropriate position with respect to the soldering area (Step ST29). This may be done by setting the component window and the soldering area in a virtual two-dimensional coordinate system in the work memory and distinguishing the distances D1 and D2 shown in FIG. 5. If it is determined that the position of the component window is not appropriate (NO in Step ST29), the set position of the component window is corrected (Step ST30) such that the positional relationship becomes correct.

If Steps ST26-ST30 are completed on all of the extracted components (YES in Step ST31), Steps ST32-ST36, which are the same as Steps ST13-ST17 explained above with reference to FIG. 4 and hence will not be described here repetitiously, are repeated for each of the components and the results of the inspection are outputted (Step ST36).

By this inspection routine, a component window can be set for each substrate such that the actual components on that substrate are included. Since the position of the component window is corrected by using the method shown in FIG. 5, even if there is a component displacement, the improper positioning of the component can be detected by correcting the component window to the position at which it should be. Thus, a highly accurate inspection can be effected according to this invention.

Although FIG. 6 shows a routine wherein the inspection of each component is carried out after the processes for identifying each component on the substrate and setting component windows are completed, this is not intended to limit the scope of the invention. Identification of components, setting of component windows and inspection may be carried out sequentially for each component.

Figure 7:
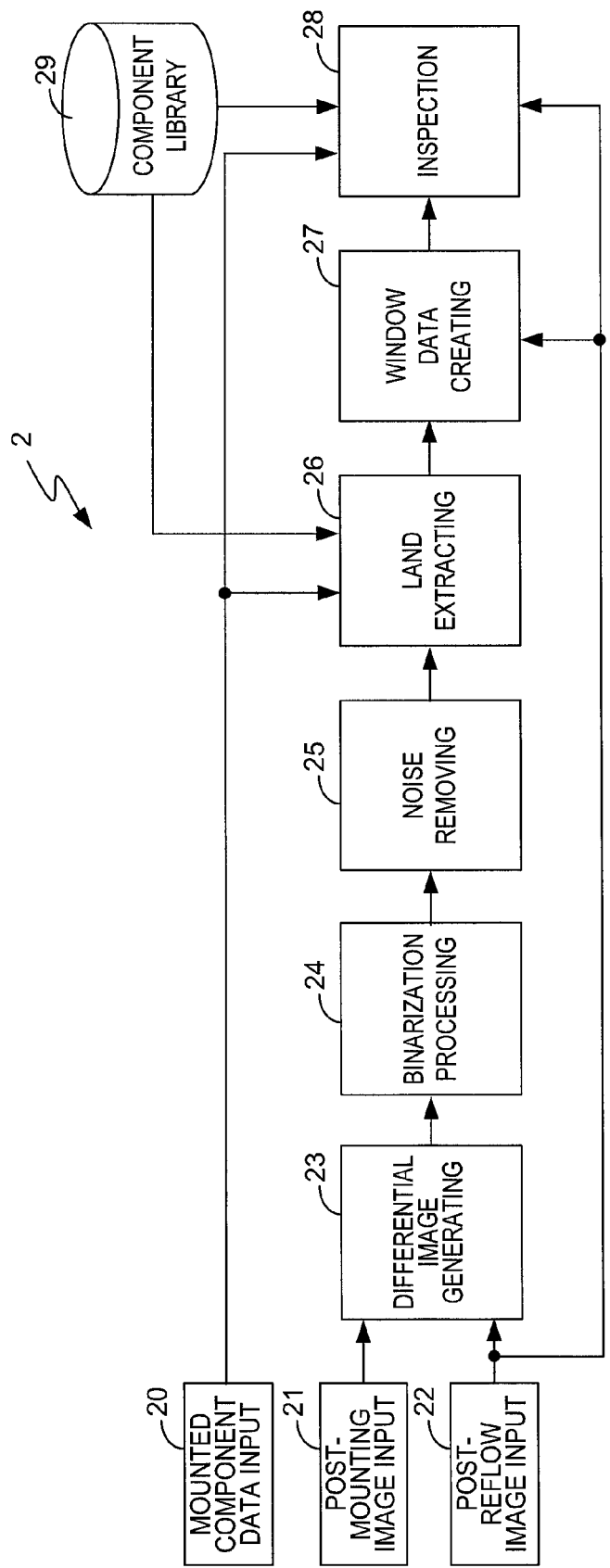
FIG. 7 is a functional block diagram of a soldering inspection apparatus embodying this invention.

FIG. 7 is a functional block diagram of a soldering inspection apparatus 2 as another embodiment of this invention, being adapted to inspect the appropriateness of the soldered condition of each component on a substrate after the soldering process in a reflow oven and comprising a mounted component data input part 20, a post-mounting image input part 21, a post-reflow image input part 22, a differential image generating part 23, a binarization processing part 24, a noise removing part 25, a land extracting part 26, a window data creating part 27, an inspection part 28 and a component library 29.

In the above, the post-reflow image means the image of the target substrate to be inspected that has undergone the soldering process in the reflow oven. According to the present example, an illumination apparatus as disclosed in Japanese Patent Publication Koho 6-1173 having light sources of the three primary colors of red, green and blue disposed at different angles with respect to the substrate is used to obtain the post-reflow image such that a color distribution depending upon the slope of the solder portion will appear on the image. The post-mounting image in the above means the image of the substrate before it is introduced into the reflow oven. The image described above which is inputted to the component inspecting apparatus 1 for inspection may be used again for the present purpose. The mounted component data are the data for showing the component positions and types specified by the component inspection apparatus 1 for each of the components on the target substrate to be inspected. The component positions are expressed by way of the setting data of the component windows and the component types are expressed by the component identification data or the variation names that are common between the component libraries 19 and 29. The inputted mounted component data are transmitted to the land extracting part 26 and the inspection part 28.

The differential image generating part 23, the binarization processing part 24 and the noise removing part 25 respectively function like the identically named parts 13, 24 and 15 of the component inspection apparatus 1 described above.

The soldering inspection apparatus 2 of this illustrated example is adapted to input a post-reflow image and a post-mounting image of a target substrate for inspection and to automatically extract from these images a window for inspecting the condition of the soldering (hereinafter referred to as the land window).

Figure 8:
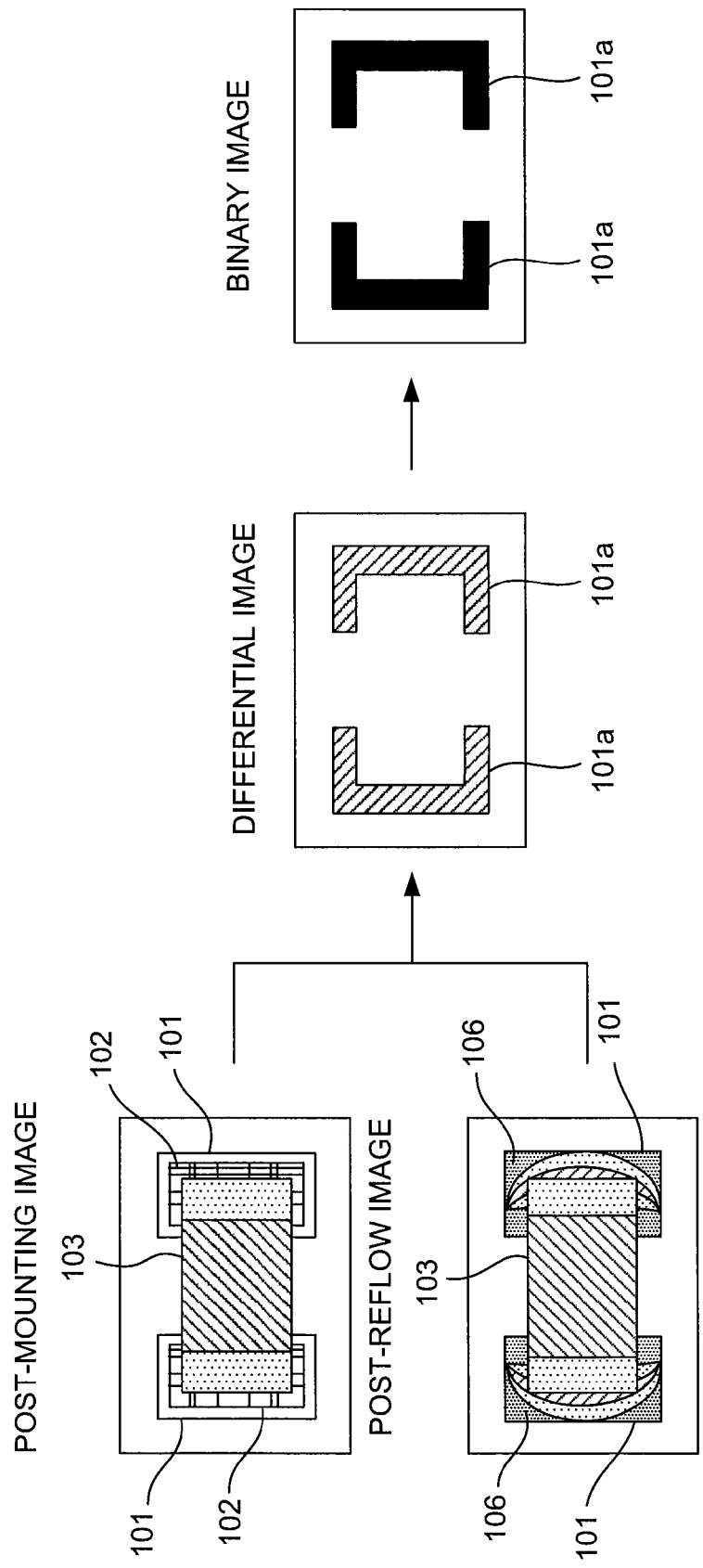
FIG. 8 shows an example of differential image and binary image obtained from a post-mounting image and a post-reflow image of a specified component.

FIG. 8 shows an example of a post-mounting image and a post-reflow image of a specified component as well as a differential image and a binary image obtained therefrom. For simplifying the representation, the differential image is shown with a uniform shading pattern although it actually has a very complicated pattern of color changes.

As the substrate is heated in the reflow oven, the cream solder on the lands is melted and then solidified, its surface becoming like a mirror surface. If an image is taken of this solder surface as it is illuminated by the aforementioned illumination apparatus, image portions as shown at 106 are obtained corresponding to the lands with a distribution of red, green and blue colors according to the slope of the reflecting surface.

The change in the colors corresponding to the surface condition of the solder is extracted from the differential image obtained from the post-mounting image and the post-reflow image. In other words, portions shown by numerals 101a corresponding to the outer edges of the lands not having any component mounted thereonto are extracted, and all pixels inside these portions 101a are converted uniformly into black pixels by a binarization process.

Based on the component positions indicated by the aforementioned mounted component data and the land data (indicative of the number and positions of the lands) read out of the component library 29, the land extracting part 26 serves to extract black pixel areas corresponding to the lands of the components from the aforementioned binary image with the noise removed. The window data creating part 27 serves to set a rectangular window, as the land window, circumscribing the aforementioned black pixel area and to transmit the setting data (indicative of the position and the size of the window) to the inspection part 28.

Based on the setting data received from the window data creating part 27, the inspection part 28 serves to set a land window on the post-reflow image for each component. The inspection part 28 also serves to read out the standard inspection data corresponding to each component, based on the component identification data in the mounted component data, and to inspect the appropriateness of the soldering condition while processing the image inside the land window according to the content that has been read out.

The method, described above, of setting a land window from the difference generated between the post-reflow image and the post-mounting image is based on the presumptions that cream solder has been properly applied onto the lands and that the melted solder remains within the confines of the lands. Since there are small fluctuations in the positions and sizes of the lands, cream solder may occasionally spill out of the land or experience displacements. In such a situation, the black pixel area extracted by the differentiation and binarization processing may not match the actual land, and the position and the size of the land may not necessarily be judged correctly.

In view of this possibility, the window data creating part 27 may be provided with the function of adjusting the size of the land window that has been set on the basis of the black pixel area. This adjustment may be effected by extracting pixels (hereinafter referred to as background pixels) having the basic color of the substrate from the post-reflow image and changing the boundary of the land window by using the result of this extraction.

Figure 9A:
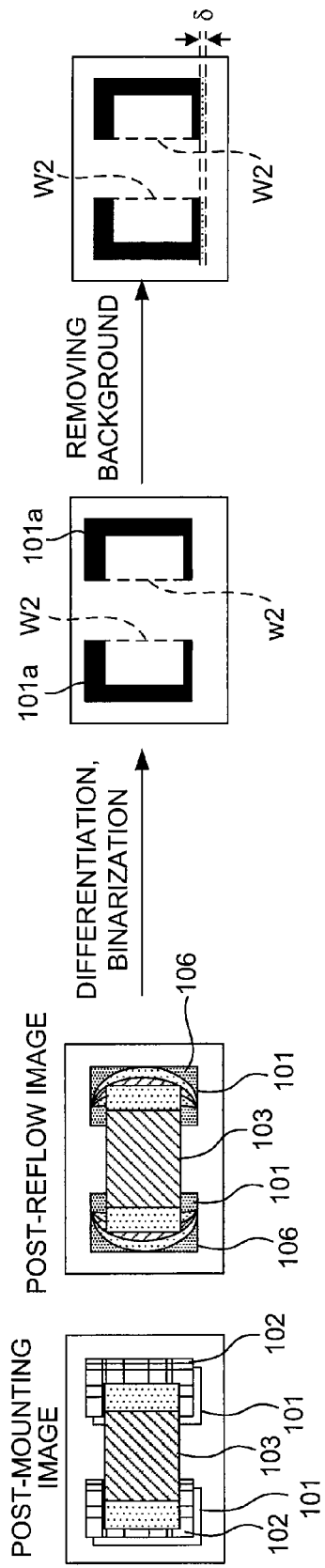
FIGS. 9A and 9B, together referred to as FIG. 9, show examples of a process for adjusting a land window.
Figure 9B:
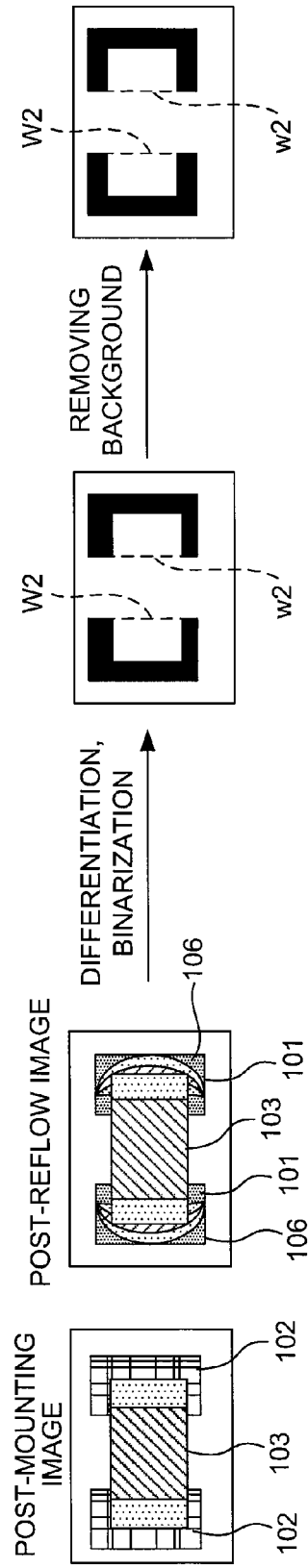

FIGS. 9A and 9B (together referred to as FIG. 9) show examples of this process of adjusting a land window. FIG. 9A shows a situation wherein cream solder 102 is displaced from a land 101 on the post-mounting image, and FIG. 9B shows another situation wherein there is too much cream solder 102 so as to completely cover a land (not shown). In the post-reflow image, however, the solder 106 is completely within the area for forming the land 101 both in FIGS. 9A and 9B because the portion of the solder spilling out of the land area has been pulled back inside by its surface tension force when it was melted during the reflow process.

If differentiation and binarization processes are effected by using such post-mounting and post-reflow images, however, black pixels are extracted also from outside the land such that the land windows W2 may be displaced as shown in FIG. 9A or may be set larger as shown in FIG. 9B.

The window data creating part 27 is therefore adapted to extract background pixels by binarizing the post-reflow image by using a threshold value determined according to the basic color of the substrate and to adjust the boundaries of the land windows W2 so as to match the boundaries of the lands 101 by eliminating pixels corresponding to the background pixels from the set land windows W2. If a specified distance δ appears, as shown in FIG. 9A, between a portion of the boundary of a window W2 (a lower edge portion according to this example) and the background pixel area due to the displacement of the window W2, it is desirable to enlarge the width of the land window in the direction of reducing this distance δ.

If an adjustment is effected as described above, land windows W2 can be set so as to correspond to actual lands. Although portions of the solder hidden by a component 103 cannot be extracted by the differentiation calculation process and hence the boundaries of the land windows W2 on the side of the component become inaccurate, this has no large effect on the inspection because the soldering inspection is primarily for the exterior, rather than the main bodies of the components.

Figure 10:
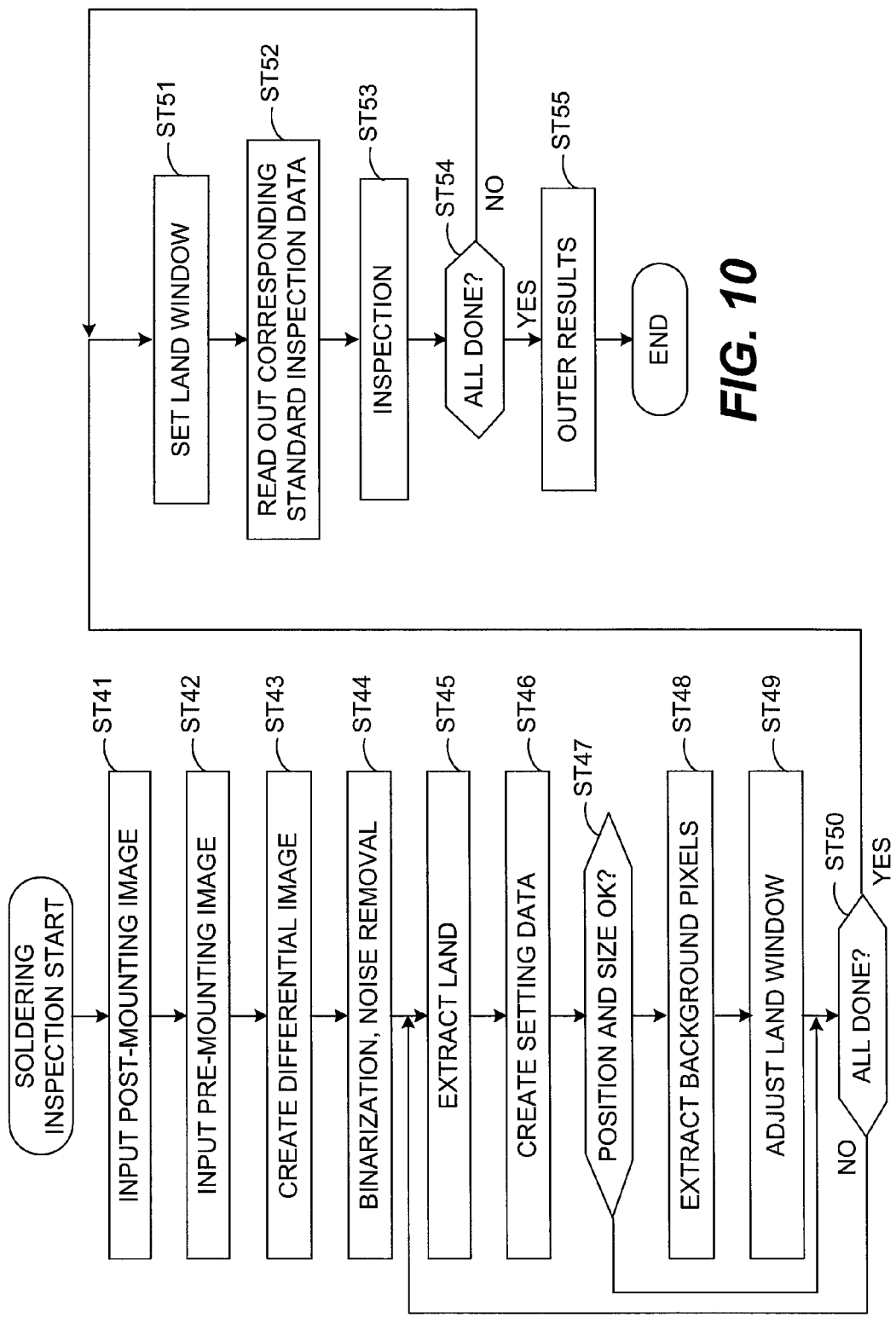
FIG. 10 is a flowchart of a routine for the soldering inspection.

FIG. 10 is a flowchart of a routine for inspecting a substrate by the soldering inspection apparatus 2 after the reflow process. The routine of FIG. 10 starts after mounted component data of the substrate type to be inspected are inputted by inputting a post-reflow image to be inspected (Step ST41) and then inputting a post-mounting image (Step ST42). The post-reflow image may be inputted from a camera 51 of the apparatus itself, and the mounted component data and the post-mounting image may be transmitted from the component inspection apparatus 1 described above.

A differential image is created from the images inputted in Steps ST41 and ST42 (Step ST43) and is binarized, and noise is removed thereafter (Step ST44). Next, Steps ST45-ST49 are repeated for each of the components, based on the mounted component data, to create setting data for land windows and to adjust their sizes.

First, the position and the type of the component under consideration are recognized from its mounted component data. A search area of a specified size is set on the binary image, based on the component position, and black pixel areas are extracted corresponding to lands in the search area. This extraction process is carried out by referencing the component library 29 based on the component type to recognize the number of lands to be extracted and the positional relationship between each land and a component and extracting a specified number of black pixel areas matching such number and positional relationship as lands of the component corresponding to the aforementioned component type (Step ST45).

Next, setting data of land windows are created for each extracted black pixel area (Step ST46). For this process, too, a window is set so as to externally circumscribe each black pixel area and data correlating the position and the size of this window with the label of a component are created.

Next, the size of the aforementioned land window and its relative position with respect to the component window are compared with the data related to the land in the aforementioned standard inspection data in order to determine whether or not there is a large positional displacement or a large difference in size (Step ST47). If it is determined that the position or the size of the set land window is not appropriate (NO in Step ST47), the aforementioned post-reflow image is binarized to extract background pixels (Step ST48) and the size of the land window is adjusted (Step ST49) on the basis of the result of extraction of the aforementioned background pixels, as explained above with reference to FIG. 9.

After Steps ST45-ST49 have been carried out on all of the components on the substrate (YES in ST 50), Steps ST51-ST53 are repeated on each of the components. Firstly, a land window is set on the post-reflow image on the basis of the set data of the component under consideration (Step ST51). Next, the standard inspection data corresponding to the component under consideration are read out from the component library 29 (Step ST52), and the soldering condition is inspected by processing the image data in the land window and evaluating the results of such processing on the basis of the standard inspection data (Step ST53).

After Steps ST51-ST53 are completed with all of the components (YES in Step ST54), the results of the inspection are outputted (Step ST55) and the process on the substrate after the reflow process is concluded.

Although the example described above shows that mounted component data are received from the component inspection apparatus 1 for each substrate, this is not intended to limit the scope of the invention. As in the example explained above with reference to FIG. 3, if the component inspection apparatus 1 serves to create and register a window setting file, the setting data of windows and component identification data in that file may be used as mounted component data. In this case, the soldering inspection apparatus 2 may be adapted to receive a window setting file from the component inspection apparatus 1 prior to the inspection and to start the inspection after registering the received file in a memory.

Inspection windows can be set corresponding to actual components and lands by processing images of an actual target substrate for inspection by using the component inspection apparatus 1 and the soldering inspection apparatus 2 described above. Thus, inspection windows can be properly set even if there are fluctuations in the positions or sizes of components or lands, and target components and soldered portions can be accurately inspected.

Although examples have been described above wherein a differential image is used to create setting data of inspection windows to be used by its own apparatus, this is not intended to limit the scope of the invention. Setting data of inspection windows to be used by a different inspection apparatus may be created.

Figure 11:
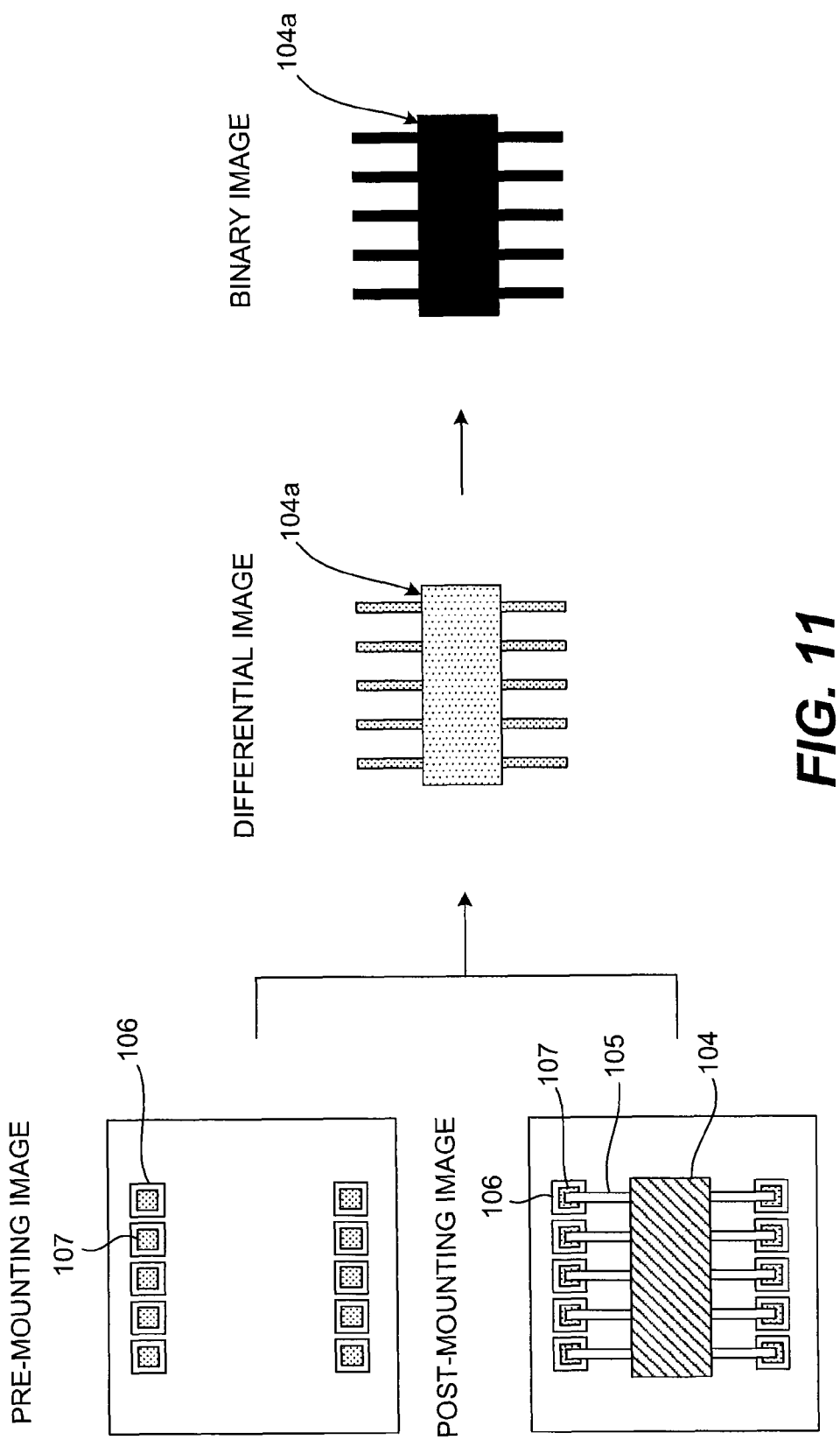

FIGS. 11 and 12 show an example wherein a lead component is the object of inspection and setting data of land windows are created by a component inspection apparatus for inspecting the soldering condition of each lead line after a reflow process. A land window is to be set for each lead in order to inspect the soldering condition of a lead component. In this example, since leads appear for the first on an image only after the component mounting process, it is the component inspection apparatus 1, and not the soldering inspection apparatus 2, that is used to create the setting data of the land windows.

In the post-mounting image of FIG. 11, numeral 104 indicates the image of a component and numeral 105 indicates that of a lead. Numeral 106 represents a land corresponding to one of the leads and numeral 107 indicates the cream solder on the land 106. In this example, too, a differential image is created from the pre-mounting and post-mounting images and is binarized to form a binary image from which an image area 104a of the whole of the component inclusive of the leads is extracted.

According to the illustrated example, tip points P0-P9 of the leads (or the images 105a thereof) are extracted from the image area 104a as shown in FIG. 12. Rectangles W0-W9 of a specified area are set, containing these tip points P0-P9 as references, and each is used as a land window. The setting data of these land windows W0-W9 are transmitted to the soldering inspection apparatus 2 and used at the time of the soldering inspection on this lead component. These tip points P0-P9 may be extracted by any known image processing method such as pattern matching.

Next, a manner in which the aforementioned component and soldering inspection apparatus 1 and 2 may be used is explained. FIG. 13 shows schematically a production line for substrates provided with a solder printer 201 for printing cream solder of a printed circuit board, a mounter 202 for mounting components onto the substrate on which solder printing has been effected and a reflow oven 203 for effecting a heating process on the substrate with components mounted thereto. A solder printing inspection apparatus 3 is provided between the solder printer 201 and the mounter 202, the component inspection apparatus 1 is provided between the mounter 202 and the reflow oven 203 and the soldering inspection apparatus 2 is provided downstream to the reflow oven 203. Conveyers (not shown) are provided between these apparatus for transporting substrates such that substrates can be processed thereby sequentially. The inspection apparatus 1, 2 and 3 are connected together through a network line 4 such as a LAN line such that they can communicate among themselves.

As shown in FIG. 14, each of these inspection apparatus 1, 2 and 3 is provided with a CCD camera 51 for generating color images and a substrate stage 53 inclusive of a mechanism for moving it two-dimensionally along an X-axis and a Y-axis. Each of the inspection apparatus 1, 2 and 3 has an illumination apparatus (not shown) near its camera 51 for illuminating the substrate. An illumination apparatus having light sources of the three primary colors is provided in particular to the soldering inspection apparatus 2.

The component inspection apparatus 1 and the soldering inspection apparatus 2 are respectively provided with the functions shown in FIGS. 1 and 7 and are each adapted to generate a target image of inspection from the substrate to be inspected and also to receive from the inspection apparatus on the upstream side (that is, the solder printing inspection apparatus 3 for the component inspection apparatus 1 and the component inspection apparatus 1 for the soldering inspection apparatus 2) the image data generated by the latter inspection apparatus at the time of its inspection. Both the received image and the image created by itself are used to create setting data of inspection windows in the manner described above and also to carry out an inspection by reading out standard inspection data correcting to each component from the component library 19 or 29. The component inspection apparatus 1 is capable of transferring to the soldering inspection apparatus 2 the setting data of component windows that were set for each of the component on an inspected substrate as the mounted component data. It is also capable of creating setting data of land windows for a specified component as shown in FIGS. 11 and 12 and transferring them to the soldering inspection apparatus 2.

The solder printing inspection apparatus 3 may be of a conventionally known structure and is adapted to process the image of a target substrate to be inspected by using standard inspection data that are preliminarily prepared for each substrate type, thereby determining appropriateness of the soldering condition at each land. The solder printing inspection apparatus 3 is further adapted to sequentially accumulate the images used for an inspection such that they can be transmitted to the component inspection apparatus 1.

For the component inspection apparatus 1 and the soldering inspection apparatus 2 to receive an image from the inspection apparatus on the upstream side, it is necessary to present a request for transmission inclusive of the identification data on the substrate that is being thereby processed. This may be done by marking individual substrates with identification data formed as a bar code or a two-dimensional code. If no substrates are to be pulled out during the course of production, numbers may be assigned serially to the substrates introduced to each of the inspection apparatus 1, 2 and 3 and these numbers may be used as their identification data.

FIG. 14 shows the common structure of the apparatus 1, 2 and 3, as comprising a control part 50 which may comprise a computer and to which are connected an image input part 52, an XY stage control part 54, an input part 55, a monitor 56 and a communication interface 58. The control part 50 may include not only a CPU but also a ROM that stores basic programs and a RAM serving as a work memory. The memory 57 is a hard disk device with a large memory capacity, storing programs related to inspection and a component library. Image data used for the inspection and inspection results are also stored in this memory 57.

The image input part 52 is inserted between the camera 51 and the control part 50 and includes an interface circuit for inputting images and an A/D converter circuit. The XY stage control part 54 serves to move the substrate stage 53 according to an instruction from the control part 50 such that the target portion to be inspected will be contained in the image-taking area of the camera 51. The input part 55 comprises a keyboard and a mouse and is used for selecting a mode of operation such as the inspection and the teaching or inputting the kind of the target substrate to be inspected at the start of an inspection. The monitor 56 is used for the presentation of a user interface at the time of a data input or the display of a target image to be inspected or the results of an inspection.

The component inspection apparatus 1 and the soldering inspection apparatus 2 can use the input part 55 to select whether or not a window setting file should be preliminarily created and registered. When an automatic inspection is carried out by using a target image to be inspected and another image received from the inspection apparatus on the upstream side without registering a window setting file, operations for selecting whether or not a correction should be made on the inspection window and specifying components to be exempted from the process of automatic setting a window. In summary, the specifications of the component inspection apparatus 1 and the soldering inspection apparatus 2 can be modified in various ways according to the level of fluctuations in the components or lands on the target substrate for inspection or the object of the user such that highly convenient inspection apparatus can be provided according to this invention.

As for inspection data other than the setting data for inspection windows, since the component inspection apparatus 1 and the soldering inspection apparatus 2 are adapted to make use of standard inspection data of a component library, an inspection can be carried out without the need to preliminarily prepare inspection data. Instead, a teaching process of a conventional kind may be carried out to create standard inspection data (or a combination of all data necessary for the inspection such as mounted positions of components, link data to inspection programs and reference values of judgments). In this example, too, a component library may be used to create standard inspection data such that setting data may be created for inspection windows by a method similar to the inspection described above and corresponding standard inspection data may be correlated.

Figure 15:
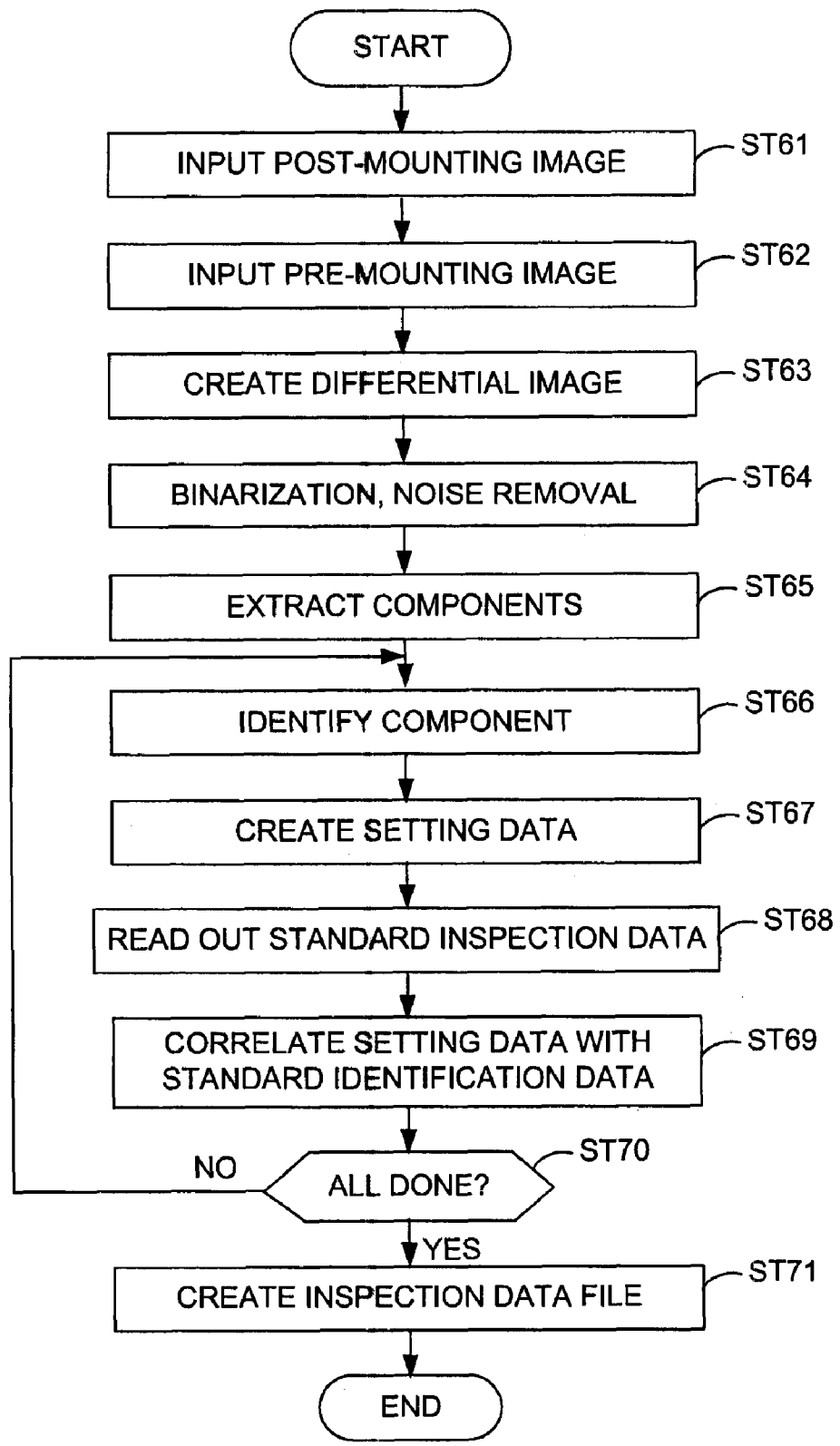
FIG. 15 is a flowchart of a routine for producing standard inspection data for component inspection.

FIG. 15 shows a routine for creating standard inspection data for the component inspection. In this process, an image is taken of a specified substrate with cream solder in a good printed condition to preliminarily obtain a pre-mounting image. Next, components are mounted to this substrate and after it is ascertained that the component is in a good mounted condition, another image is taken to obtain a post-mounting image. Steps ST61-ST65 of this routine are similar to Step ST1-ST5 of FIG. 3 and each component on the substrate is thereby extracted. Steps ST66-ST69 are thereafter repeated for each component to create inspection data.

First, the size of the component under consideration is compared with the size data of each variation in the component library 19 such that the component is identified (Step ST66) as done in Step S6 of FIG. 3. Next, setting data of component windows are created for the component under consideration (Step ST67) by a method similar to Step ST7 of FIG. 3. Next, the standard inspection data of the component identified in Step ST66 are read out from the component library 19 (Step ST68) and inspection data corresponding to the component under consideration are set by correlating the data that have been read out with the standard inspection data (Step ST69).

Thereafter, inspection data are created for each component by combining setting data of component windows created from the image of an actual substrate and standard inspection data. The created inspection data are temporarily saved in the work memory.

When Steps ST66-ST69 are completed for all of the components (YES in Step ST70), an inspection data file is created by collecting the inspection data of each component that are temporarily saved and is registered in the memory 57 (Step ST71).

In the above, where the standard detection data are created, and especially where the setting data of component windows are created, it is desirable to use a plurality of substrates, to create data for each of them and to use as the final setting data the average of these data.

By this process for creating inspection data, not only can the position and size of each component be extracted easily by using a pre-mounting image and a post-mounting image, but each component can also be identified on the basis of its size. Standard data of the component library can also be correlated. Thus, the cumbersome process of correlating components and standard data as in the conventional method of using CAD data can be eliminated and inspection data can be created efficiently according to this invention. In the case of components that cannot be identified easily from size data, however, it is desirable to handle separately, say, by causing the user to select the type of the component.

For the soldering inspection, too, standard inspection data can be created by first creating setting data of land windows by a routine similar to Steps ST41-ST46 of FIG. 10 and then combining these setting data with standard inspection data corresponding to the component. Both for the inspection of mounted components and soldering condition, inspection data may be created by means of a device other than an inspection apparatus such as a personal computer and introduced to the inspection apparatus 1 and 2 shown in FIGS. 1 and 7.

The disclosure provided herein is intended to be interpreted broadly. In particularly, where a description was provided in a singular form, situations which should be described in a plural form are intended to be included. This is in accordance with the provision in 1 U.S.C. 1.

What is claimed is:

1. A method for creating inspection data for inspecting a substrate, said method comprising:

a first step of registering, in a tangible medium readable by a computer, standard inspection data including size data of components of various types, components with only small differences in external appearances being collected in a group referred as a variation having an assigned variation name as identification data;

a second step of taking and thereby obtaining a first image of said substrate before components are mounted to said substrate;

a third step of taking and thereby obtaining a second image of said substrate after components are mounted to said substrate;

a fourth step of generating a differential image between said first image and said second image obtained in said second step and said third step, extracting black pixel areas by binarization of said generated differential image, extracting a number of constituent pixels of said black pixel areas per each component as an extracted size data for each component, comparing said size data in said standard inspection data and thereby identifying a corresponding component by using the variation name;

a fifth step of setting said component identified in said fourth step as component identifying data;

a sixth step of determining setting conditions for a window based on position and size of area where the corresponding component was identified in said fourth step and registering as said inspection data by combining said component identifying data and said determined setting conditions; and a seventh step of saving in a work memory a corresponding variation name which corresponds to said identified corresponding component;

wherein said second step, said third step, said fourth step, said fifth step and said sixth step are carried out by said computer using a program that is incorporated in said tangible medium.

2. The method of claim 1 wherein said standard inspection data are registered in a component library in a component inspection apparatus.

3. An apparatus for inspecting mounting conditions of components on a substrate, said apparatus comprising:

memory means for registering standard inspection data inclusive of size data of each type of said components, components with only small differences in external appearances being collected in a group referred as a variation having an assigned variation name as identification data;

a first image input means for inputting a post-mounting image of said substrate after components are mounted to said substrate;

a second image input means for inputting a pre-mounting image of said substrate before said components are mounted to said substrate;

component extracting means for generating a differential image between said pre-mounting image and said post-mounting image inputted by said first image input means and said second image input means for a specified substrate, extracting black pixel areas by binarization of said generated differential image, extracting the number of constituent pixels of said black pixel areas per each component as an extracted size data for each component, comparing said size data in said standard inspection data and thereby extracting an area corresponding to each of said components by using the variation name;

teaching means for carrying out a teaching process for inspection based on said corresponding area extracted by said component extracting means and said standard inspection data, said teaching process including saving a corresponding variation name which corresponds to said identified component type; and inspection processing means for carrying out an inspection, when a post-mounting image of a substrate with same structure as said specified substrate is inputted by said first image input means, on said inputted post-mounting image;

wherein said teaching means carries out, on said extracted corresponding area, the steps of:

identifying the component type of the corresponding component by comparing the size of the corresponding area with the size data in said standard inspection data by using the variation name;

creating window setting data for a window for component inspection based on the position and the size of said corresponding area; and combining and registering in said memory means as registered combinations component identifying data for indicating said identified component type and said window setting data; and wherein said inspection processing means carries out, for all of the registered combinations, the steps of:

setting said window for component inspection on an inputted image to be inspected based on window setting data included in specified one of the combinations registered in said memory means; and inspecting an image within said window for component inspection by using the standard inspection data corresponding to the component identifying data in said specified one registered combination.

4. A method for inspecting component-mounting conditions of a substrate, said method comprising the steps of:

registering for each component type standard inspection data inclusive of size data of each component type in a tangible medium readable by a computer, components with only small differences in external appearances being collected in a group referred as a variation having an assigned variation name as identification data;

carrying out a teaching process by using said standard inspection data and an image of a specified substrate; and carrying out an inspection process on a substrate having the same structure as said specified substrate by using data registered by said teaching process and said standard inspection data after carrying out said teaching process;

wherein said steps of carrying out said teaching process and said inspection process are carried out by said computer by using a program incorporated in said tangible medium readable by said computer;

wherein said teaching process comprises:

obtaining a pre-mounting image and a post-mounting image of said specified substrate respectively before and after components are mounted on said specified substrate;

generating a differential image between said pre-mounting image and said post-mounting image and extracting black pixel areas by binarization of said generated differential image, extracting number of constituent pixels of said black pixel areas per each component as an extracted size data for each component; and carrying out, for each of the extracted area corresponding to each component, the steps of:

identifying the component type of the corresponding component by comparing the black pixel numbers with the size data in said standard inspection data by using the variation name;

creating window setting data for a window for component inspection based on the position and the size of said corresponding area;

combining and registering as registered combinations component identifying data for indicating said identified component type and said window setting data; and saving in a work memory a corresponding variation name which corresponds to said identified component type; and wherein said inspection process comprises:

obtaining an image of a target substrate after components are mounted thereon; and carrying out, for all of the registered combinations, the steps of:

setting a window for component inspection on said obtained image based on window-setting data contained in specified one of the combinations registered in said teaching process; and inspecting an image within said window for component inspection by using the standard inspection data corresponding to the component identifying data in said specified one registered combination.

5. The method of claim 4 wherein said standard inspection data are registered in a component library in a component inspection apparatus.

* * * * *